United States Patent [19]
Culver et al.

[11] Patent Number: 6,045,789
[45] Date of Patent: Apr. 4, 2000

[54] BYSTANDER EFFECT TUMORICIDAL THERAPY BY EXPRESSING AN HSV-TK GENE

[75] Inventors: Kenneth W. Culver, Potomac; R. Michael Blaese, Rockville, both of Md.

[73] Assignee: The United States of America as represented by the Secretary of the Department of Health and Human Services, Washington, D.C.

[21] Appl. No.: 08/274,584

[22] Filed: Jul. 13, 1994

Related U.S. Application Data

[63] Continuation of application No. 07/877,519, May 1, 1992, abandoned.

[51] Int. Cl.$^7$ .......................... A61K 48/00; C12N 15/00
[52] U.S. Cl. ................. 424/93.21; 424/93.2; 424/93.6; 435/320.1
[58] Field of Search .................. 424/93.2, 93.21; 435/172.3, 69.3, 69.5, 69.51, 69.52, 320.1; 514/44; 935/14, 32, 57, 65.71

[56] References Cited

U.S. PATENT DOCUMENTS

| | | | |
|---|---|---|---|
| 5,358,866 | 10/1994 | Mullen et al. | 435/240.2 |
| 5,529,774 | 6/1996 | Barba et al. | 424/93.21 |
| 5,601,818 | 2/1997 | Freeman et al. | 424/93.21 |

FOREIGN PATENT DOCUMENTS

0476953A3   3/1992   European Pat. Off. .

OTHER PUBLICATIONS

Moolten, 1990. Critical Reviews in Immunology. 10(3):203–233.

Gansbacher et al., Cancer Res. 50 (Dec. 15, 1990), pp. 7820–7825.

Tepper et al., Cell, vol. 57 (May 5, 1989), pp. 503–512.

Asher et al., J. Immunol. vol. 146, No. 9 (May 1, 1991) pp. 3227–3234.

Yannelli et al., J. Immunol., vol. 135, No. 2 (Aug. 1985) pp. 900–905.

St. Clair et al., Antimicrob. Ag. Chemother, vol. 31, No. 6 (Jun. 1987) pp. 844–849.

Fearon et al. Cell, vol. 60 (Feb. 9, 1990) pp. 397–403.

Gansbacher, J. Exp. Med. vol. 172 (Oct. 1990) pp. 1217–1224.

Moolten, Cancer Res. 46 (Oct. 1986) pp. 5276–5281.

Orkin & Motulsky, Dec. 7, 1995. "Report and Recommendations of the Panel to Assess the NIH Investment in Research on Gene Therapy", National Institutes of Health, USA.

*Primary Examiner*—Deborah Crouch
*Attorney, Agent, or Firm*—Klarquist Sparkman Campbell Leigh and Whinston, LLP

[57] ABSTRACT

A method for treating an tumor involves the initial identification of the tumor as one displaying a "bystander effect," whereby in vivo transfer of a gene conferring sensitivity to chemotherapeutic agent affects both transformed and non-transformed tumor cells. Into a tumor thus characterized is introduced in situ a retroviral vector containing the sensitizing gene. The retroviral vector, which may replication-defective or replication-competent, can be introduced directly (if it is replication-competent) or can be provided by means of a packaging cell line. Treatment of the patient with the chemotherapeutic agent thereafter effects tumor regression when as few as 10% of tumor cells are transformed, while normal tissue is not damaged. The anti-tumor impact of the treatment can be increased when the transducing vector also encodes an immune response-enhance substance such as IL-2 or another cytokine.

5 Claims, 2 Drawing Sheets

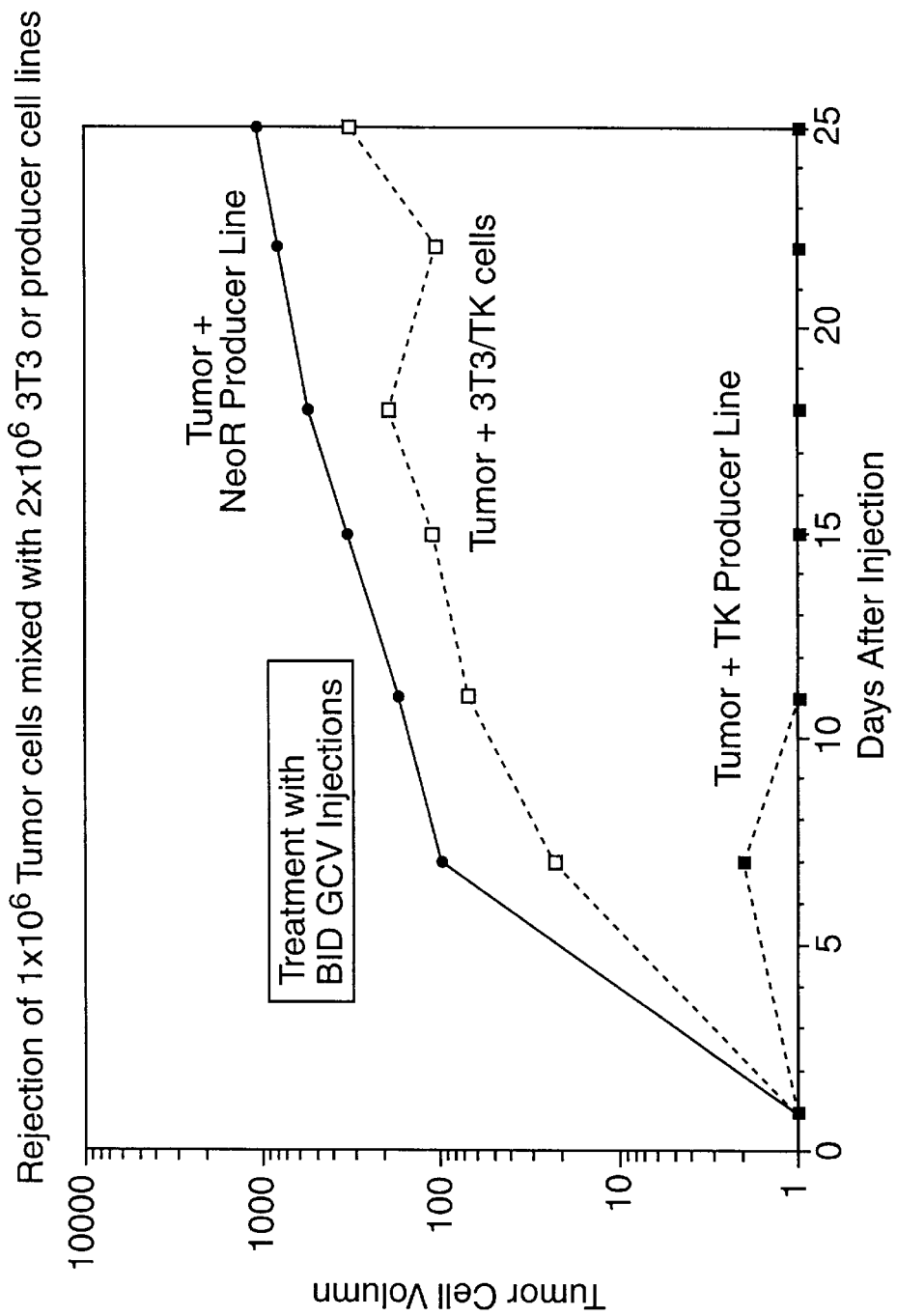
FIG. 2  3T3/TK contains the NeoR & TK genes, but produced no infectious vector. The TK and NeoR producer lines contain the genes and make infectious vector capable of transferring the genes to adjacent tumor tissue.

BYSTANDER EFFECT TUMORICIDAL THERAPY BY EXPRESSING AN HSV-TK GENE

This application is a continuation of application Ser. No. 07/877,519, filed May 1, 1992, now abandoned.

BACKGROUND OF THE INVENTION

The present invention relates to an approach to cancer therapy which entails gene transfer in vivo.

Gene transfer has been recognized for some time as a promising avenue to therapies for cancers, among other diseases. The earliest applications of gene transfer for cancer treatment have been indirect approaches focusing on enhancing anti-tumor immune responses. Thus, for instance, attempts have been made to increase the cytotoxicity of immune cells, or to enhance their proliferation.

In one such approach, the gene for tumor necrosis factor (TNF) was inserted into tumor infiltrating lymphocytes (TIL) in an attempt to use the homing properties of TIL to deliver the toxic gene product preferentially to the tumor in situ. Initiation of this protocol has been difficult, however, because transduced T-cells shut down vector cytokine expression. Rosenberg et al., *Human Gene Therapy* 1: 443 (1990).

By another approach, tumor cells have been modified in vitro with cytokine genes and reintroduced into patients in an attempt to immunize the patient to their own cancer. In animal studies, the IL-4 gene was introduced to tumors by Tepper et al., *Cell* 57: 503 (1989); the IL-2 gene by Fearon et al., *Cell* 60: 397 (1990), and by Gansbacher et al., *J. Exp. Med.* 172: 1217 (1990); the interferon-gamma gene by Gansbacher et al., *Cancer Res.* 50: 7820 (1990); and TNF gene by Asher et al., *J. Immunol.* 146: 3227 (1991). Each of the animal studies demonstrated rejection of genetically altered tumors upon reimplantation, and the mice in these studies were immune to subsequent rechallenge with the same tumor.

Rosenberg and co-workers have carried out similar experiments in humans using the TNF gene and the IL-2 gene, respectively, with encouraging results. See Rosenberg et al., *Human Gene Therapy* 3: 57, 75 (1992).

These early investigations of the clinical use of gene transfer required that the tumor be excised and TIL or tumor cell lines established in culture which then could be gene-transduced in vitro and subsequently reimplanted into the patient. This approach is complicated, expensive, and limited by the fact that TIL and tumor lines cannot be regrown in vitro from the tumors of all patients and by the necessity to perform ex vivo transduction.

Retroviral vectors currently provide the most efficient means for ex vivo gene transfer in the clinical setting, but their usefulness has been seen as limited because retroviruses stably integrate only in target cells that are actively synthesizing DNA, and integration is a prerequisite to retroviral gene expression. Thus, attempts to use retroviruses to transfer genes into cell types that, as a population, are in $G_o$, such as totipotent bone marrow stem cells, have had only limited success.

Cancers consist of actively replicating cells, however, and are often surrounded by quiescent normal cells. Thus, the above limitation may be exploited as an advantage in treating cancers, since a retroviral vector that carries a therapeutic agent would be integrated and expressed preferentially or exclusively in the cells of the cancerous mass.

In this regard Ezzeddine et al., *New Biologist* 3: 608–14 (1991), have reported on the use of retroviral vector-mediated gene transfer in vitro in an attempt to treat tumors. More specifically, a murine retroviral vector was employed to introduce a thymidine kinase gene from herpes simplex virus 1 ("HSV-1 tk gene") into C6 rat glioma-derived cell lines in vitro. Cells which had taken up the retroviral vector and expressed the tk gene were sensitized to the anti-viral agent ganciclovir, and were preferentially killed when exposed to ganciclovir in the medium.

Ezzeddine et al. were able to use the method to define conditions in vitro for killing essentially all infected cells but not uninfected cells. In addition, C6 cells were introduced subcutaneously into nude mice to form tumors and the tumor-bearing mice were treated with ganciclovir. Ganciclovir inhibited the growth of tumors formed by HSV-1 tk expressing C6 cells, but did not affect tumors formed by HSV-1 tk C6 cells.

Ezzeddine et al. thus showed that in vitro retroviral gene transfer can be used to sensitize cells to a cytotoxic agent, which can then be used to kill the cells when they are propagated as tumors in nude mice. The authors did not demonstrate any practical way to introduce an HSV-1 tk gene into tumor cells in situ, however. Ezzeddine et al. also did not show how to eradicate all neoplastic cells, a prerequisite for tumor remission, when less than all cells in the tumor would take up a tk gene, express the gene at a level sufficient to assure conversion of the drug to toxic and, as a consequence, be killed by exposure to ganciclovir.

Short et al., *J. Neurosci. Res.* 27: 427–33 (1990), have described the delivery of genes to tumor cells by means of grafting a retroviral vector-packaging cell line into a tumor. The packaging cell line produced a replication-defective retroviral vector in which the MoMLV LTR promoter-operator was used to drive expression of β-galactosidase, which served as a marker of retroviral vector propagation. When the packaging cell line was grafted into a tumor, β-galactosidase expression in situ was seen only in packaging cells and in proliferating tumor cells, not in normal tissue.

Despite the apparent preference for tumor cells, propagation of the retroviral vector from producer cells to tumor cells was relatively inefficient, according to Short et al., and only a fraction of the cells in the tumor were infected. Furthermore, practically no β-galactosidase expression was observed when cell-free retroviral vector particles were introduced to a tumor directly rather than in a packaging cell line. Short et al. opined that a packaging cell line might be used to deliver a "killer" or "suppressor" gene to tumor cells, but observed an efficiency of infection far below what would be required for therapeutic utility based on direct gene transduction into all the cells of a tumor.

SUMMARY OF THE INVENTION

It is therefore an object of the present invention to provide a effective method for gene transfer-based cancer treatment.

It is a further object of the present invention to provide a method of using retroviral vector gene-transfer in situ to render cancer cells sensitive to an agent that ordinarily does not affect mammalian cells.

In accomplishing these and other objects, there has been provided, in accordance with one aspect of the present invention, a method for in situ treatment of a tumor, comprising the steps of (a) characterizing a tumor as one that exhibits a bystander effect; (b) transforming cells of the tumor in situ with a polynucleotide such that the cells express the polynucleotide, the polynucleotide comprising a first nucleotide sequence which, when expressed in the cells, confers sensitivity to a chemotherapeutic agent; and thereafter (c) treating the tumor with the chemotherapeutic agent. In a preferred embodiment, step (b) comprises introducing into the tumor either (i) a replication-competent retroviral vector containing the polynucleotide or (ii) a cell line that produces a retroviral vector containing the polynucleotide. In another preferred embodiment, step (a) comprises the use of a retroviral vector, for transforming the tumor cells, that further comprises a second nucleotide sequence coding for an immune response-enhancing substance, such as a cytokine or an immune co-activating signal molecule.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2 is a graph showing the elimination of tumors in ganciclovir-treated mice bearing fibrosarcomas derived from mixtures of one million tumor cells and two million HSV-tk retroviral vector-producing fibroblasts.

DETAILED DESCRIPTION OF PREFERRED EMBODIMENTS

Figure 1:
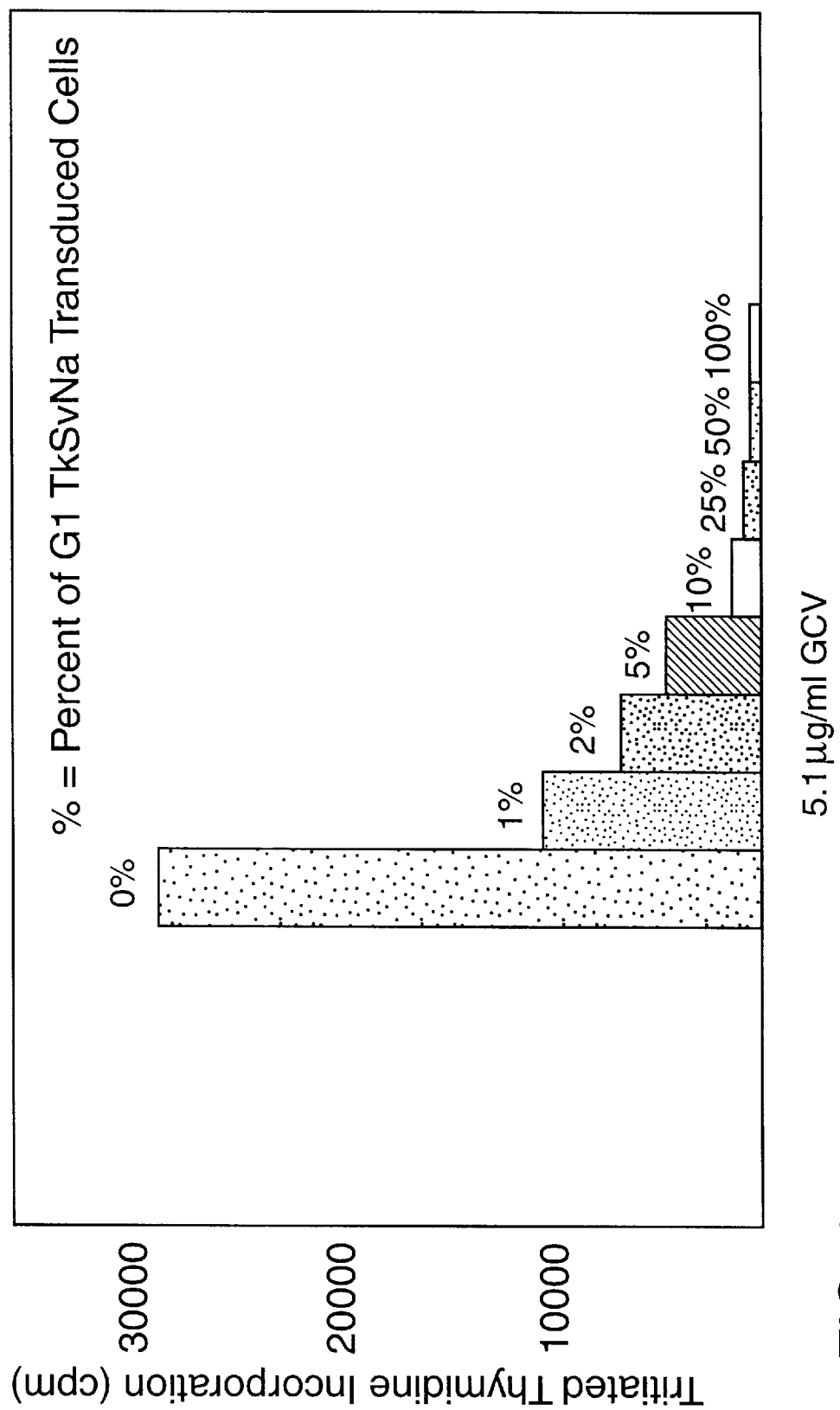
FIG. 1 is a graph that displays the effect of ganciclovir exposure on the incorporation of tritiated thymidine by different populations of cultured cells, each population representing a different mixture of cells transduced in accordance with the present invention and non-transduced cells. A very significant effect of the ganciclovir is evident when only 1% of the cultured cells are transduced, reflecting the impact of a bystander effect.

Notwithstanding previous failed attempts to develop a cancer therapy based on gene transfer, an approach has been discovered for treating cancer effectively by retroviral vector mediated gene transfer in vivo. A key to the success of the new approach is the recognition that certain tumors exhibit a "bystander effect" which had not been identified previously. More specifically, it has been discovered that, in tumors that exhibit a bystander effect, the transformation of tumor cells in vivo with a polynucleotide molecule (hereafter, "the sensitizing gene"), which gene renders a host cell sensitive to a chemotherapeutic agent, affects not only transduced cells but also non-transduced cells as well.

For such tumors, in other words, neoplastic cells which appear not to have been transformed genetically nevertheless display enhanced sensitivity to a pharmacological agent, sensitivity to which is imparted to neighboring cells that are transformed, generally by means of retroviral vector, and that express the sensitizing gene. Identifying a tumor as one that displays such a bystander effect is the departure point, pursuant to the present invention, for a treatment to eradicate all tumor cells and not just those transformed by the retroviral vector. A further major advantage of this approach is that normal cells in the tissue surrounding the cancer are largely unaffected by the therapy because these cells are most often in $G_o$ phase (are not dividing) and, hence, are not infected by the retroviral vector. Moreover, the retroviral vector and cells producing it are eliminated from the patient along with the tumor, because any cell containing the retroviral vector will be sensitive to the cytotoxic agent.

Pursuant to the present invention, therefore, a patient receives a sensitizing agent-encoding gene which is introduced into a tumor that has been determined to exhibit a bystander effect. Tumor cells are transformed with the gene via the introduction into the tumor of a gene-containing retroviral vector per se or of producer cells which express the retroviral vector as free viral particles. The retroviral vector may be incapable of replication or it may be replication competent. By means of the retroviral vector, the sensitizing gene is transferred to some but not necessarily all cells of the tumor.

Expression of the gene in the tumor cells results in production of functional sensitizing agent in the tumor. In accordance with the present invention, the patient then is exposed to an anti-tumor agent that is cytotoxic to cells which express the sensitizing gene, resulting in death of those cells. By virtue of the bystander effect, the anti-tumor agent is cytotoxic as well to tumor cells that have not taken up retroviral vector and do not express the sensitizing gene.

Tumors which occur in tissues composed of quiescent cells can be treated, for example, in accordance with the present invention. In another embodiment, a tumor is treated that occurs at site, such as in the brain, that is immunologically privileged, i.e., where the immune system is more tolerant of the presence of the retroviral vector or vector-producing cells. In yet another embodiment, cells of a targeted tumor are transformed with a second gene, expression of which enhances immune response to the tumor.

Identifying Tumors that Exhibit a Bystander Effect:

As mentioned above, transformation and subsequent treatment are targeted in the present invention to tumors that exhibit a bystander effect. Screening tumors for a bystander effect can be carried out as described below, following preferred methodology of the invention.

First, a sample is obtained of a tumor in which the bystander effect is to be determined. Cells from the sample are cultured in vitro, whenever possible. Cultured cells are transduced in vitro with a retroviral vector to express a sensitizing gene that confers sensitivity to some agent. The transduced cells are co-cultivated with control cells of the same line that are not transformed or that have been transduced with a vector which is incapable of directing expression of the sensitizing gene. The resulting mixture of sensitive and non-sensitive cells then are exposed to the agent, so that the cytotoxic effect of the agent on both types of cells can be determined, for example, by measuring the uptake of $^3$H-thymidine (an indicator of cell replication) or by assessing cell-viability.

A bystander effect is detected when tumor cells which express the sensitivity-conferring gene and tumor cells which do not reflect the impact of exposure to the agent. Conversely, when a tumor which does not exhibit the bystander effect is tested, cytotoxicity will be limited to cells expressing the sensitivity-conferring gene, i.e., in mixed cultures the agent will not affect control cells. FIG. 1 is illustrative of results, obtained in vitro for a particular human melanoma, that reflect the incidence of a bystander effect.

Mixtures of tumor cells and transformed, sensitizing gene-expressing cells also can be introduced into a nude mouse or another immunologically compromised test animal, such as a SCID mouse or a BNXID mouse, and propagated as a tumor. This will be possible for some types of cells that cannot be cultivated in vitro but will not be possible for all in vitro cell lines. After administration of the appropriate agent, the bystander effect can be determined by observing tumor regression, or continued tumor growth. When tumor regression is observed in this assay, biopsy samples of the tumor may be obtained and examined by histological, cytological or other techniques to determine whether changes in tumor size reflect the death of only cells expressing the sensitizing gene or of both types of cells, the latter circumstance evidencing a bystander effect.

In a preferred embodiment, an HSV-tk gene is used to confer sensitivity to the anti-viral agent ganciclovir. Thus, cells from a tumor to be tested for the bystander effect are propagated in vitro, as described above. Propagation can be carried out in any culture system suitable to cultivating cells of the tumor to be treated. In preferred embodiments in vitro culture is carried out in plastic cultureware plates, flasks, roller bottles and the like, by means well-known in the art. See ANIMAL CELL CULTURE: A PRACTICAL APPROACH (IRL Press 1986). A retroviral vector carrying the HSV-tk then is transduced into the cells to establish cell lines which express the tk gene and are sensitive to ganciclovir.

In many instances it will be desirable to introduce a selectable marker into target cells along with the HSV-tk gene, thereby to facilitate establishment of transformed cells lines. The co-transformed cells will be cultured under selective conditions to establish stably transformed HSV-tk expressing and/or retroviral vector producing, HSV-tk expressing cells. The NeoR gene, which confers resistance to G418, is one of several selectable marker genes known to the art which are preferred for establishing stably transformed cells lines in accordance with the present invention.

The bystander effect then is assayed by determining the effect of ganciclovir on mixtures of stably transformed tumor cells which express HSV-tk and cells that do not express HSV-tk. The effects of ganciclovir on the HSV-tk-expressing cells and non-expressing cells in the mixed culture are compared. Cytotoxicity to non-transduced/non-expressing cells is evidence of the bystander effect and, hence, of the suitability of the tumor for treatment in accordance with the present invention.

Alternatively, the susceptibility of a given tumor to the bystander effect can be assayed, even without transforming cells of the tumor, by co-cultivating tumor cells with cells of a tk$^+$ cell line which has been determined to display a bystander effect. If the test cells from the tumor are affected when the mixture of both cell types is exposed to ganciclovir, the conclusion is readily drawn that the tumor cells indeed are susceptible to the bystander effect "received," so to speak, from the tk$^+$ cells.

It also will be appreciated that tumor cells in some cases may be propagated in nude mice or other immunologically compromised test animals and tested in situ for the bystander effect in much the same way discussed above. This expediency would be limited to the extent that the tumor under study must be amenable to propagation in the animal.

Retroviral Vectors and Packaging Cell Lines:

In accordance with the present invention, a variety of retroviral vectors and retroviral vector-producing cell lines can be used to impart, inter alia, an appropriate sensitivity to a tumor. Retroviral vectors suitable in this context include replication-competent and replication-defective retroviral vectors. Amphotropic and xenotropic retroviral vectors can be used. In carrying out the invention, retroviral vectors can be introduced to a tumor directly or in the form of free retroviral vector-producing cell lines.

To engender production of a sensitizing activity, a retroviral vector employed in the present invention must integrate into the genome of the host cell, an event which occurs only in mitotically active cells. The necessity for host cell replication effectively limits retroviral gene expression to tumor cells, which are highly replicative, and to a few normal tissues.

The normal tissue cells most likely in theory to be transduced by a retroviral vector are the endothelial cells which line the blood vessels supplying blood to the tumor. In addition, it is also possible that a retroviral vector would integrate into white blood cells both in the tumor or in the blood circulating through the tumor. This appears not to occur, however, at least in experimental animals (see EXAMPLE 5 below). The spread of retroviral vector to normal tissues thus is limited. Retroviral vector integration into normal tissue also does not pose a problem, with regard to propagation of deleterious retroviral vector in a patient, because integration and concomitant expression of sensitizing activity results in elimination of all such transduced cells. Moreover, local administration to a tumor of retroviral vector or retroviral vector-producing cells will restrict vector propagation to the local region of the tumor, minimizing transduction, integration, expression and subsequent cytotoxic effect on surrounding cells that are mitotically active.

Both replicatively deficient and replicatively competent retroviral vectors can be used in the invention, subject to their respective advantages and disadvantages. For instance, for tumors that have spread regionally, such as lung cancers, the direct injection of cell lines that produce replication-deficient vectors may not deliver the vector to a large enough area to completely eradicate the tumor, since the vector will be released only from the original producer cells and their progeny, and diffusion is limited.

Similar constraints apply to the application of replication deficient vectors to tumors that grow slowly, such as human breast cancers which typically have doubling times of 30 days versus the 24 hours common among human gliomas. The much shorted survival-time of the producer cells, probably no more than 7–14 days in the absence of immunosuppression, limits to only a portion of their replicative cycle the exposure of the tumor cells to the retroviral vector.

In these and like circumstances, the injection of replication-competent retroviral vector particles or a cell line that produces a replication-competent retroviral vector virus would be more effective because a replication-competent retroviral vector will establish a productive infection that will transduce cells as long as it persists. Moreover, replicatively-competent retroviral vectors may follow the tumor as it metastasizes, carried along and propagated by transduced tumor cells.

The risks for complications are greater with replicatively competent vectors, however. Such vectors may pose a greater risk of transducing normal tissues than do replicatively deficient vectors, for instance. As discussed above, the suicidal nature of the HSV-tk/ganciclovir system, for example, limits these side effects. For each given tumor and affected body area, the risks of undesired vector propagation and concomitant damage to normal tissue due to either transduction itself or ganciclovir-mediated cytotoxicity will be weighed against the advantages of replicatively competent versus replicatively deficient retroviral vector.

In principle, any retrovirus can be used as a vector in the present invention if the virus is dependent on proliferating target cells for integration. Thus, both amphotropic and xenotropic retroviral vectors may be used. Amphotropic virus have a very broad host range that includes most or all mammalian cells, as is well known to the art. Xenotropic viruses can infect all mammalian cell except mouse cells. Thus, amphotropic and xenotropic retroviruses from many species, including cows, sheep, pigs, dogs, cats, rats and mice, inter alia, can be used to provide retroviral vectors in accordance with the invention, provided the vectors can transfer genes into proliferating human cells in vivo.

Control Signals:

Vectors used in the present invention generally are engineered retroviral genomes which provide for expression of a cloned gene or genes upon their introduction into a cell. Thus, suitable retroviral vectors provide the control signals necessary for transcription of a cloned gene in the particular cells of a target tumor or in cells to be introduced into the tumor. Control signals that are effective in virtually all eukaryotic cells often may be useful in this regard. Many such control signals are known in the art. See Hock et al., Blood 74: 876–81 (1989). In other instances it may be desirable to use more specialized control sequences.

Among the important control elements are promoters. Promoters suitable for use in the invention include any promoter that can provide transcription of a sensitizing gene or, adjunctively, an immune response-enhancing gene, inter alia, in the cells of a tumor to be treated and/or in a feeder cell line to be used for treatment. A variety of promoters suitable to this purpose are well known, including inducible and constitutive promoters and viral and cellular promoters. In accordance with conventional techniques, the promoters can be operably linked to a gene to be expressed to make a construct which, when introduced into a cell, provides for transcription of the gene. By the same token, other cis-acting controls, such as enhancer sequences, operator sequences and the like, as well as a ribosome binding site, an initiation codon and transcription termination and polyadenylation signals, also can be operably linked to a gene or genes to be expressed.

A promoter that is exclusively or more efficiently active in tumor cells then in normal proliferative tissue can be advantageously employed in the present invention. Promotors for the cellular proto-oncogenes are likely to be useful in this respect, as their activity in many instances is elevated in tumor cells. Tissue specific promoters also may be useful in this context, particularly those like the α-fetoprotein promoter which normally is inactive in an adult but which is activated in certain cancers. Tumor cell-specific promoters such as these are particularly advantageous because they can target expression of a sensitizing gene, inter alia, specifically to tumor cells, thereby avoiding cytotoxic side effects in normal cells transduced by the vector that express the gene, where such side effects are engendered by substances generated by the sensitizing gene in the affected cell.

Sensitizing Genes:

A variety of genes can be included in a retroviral vector and used, in accordance with the present invention, to render cells sensitive to an agent which ordinarily is non-toxic to mammalian cells, such as an antimicrobial or antiviral drug. Preferably the gene renders the tumor uniquely sensitive to a drug that ordinarily is not toxic to the target organ or to the body in general.

In a particularly preferred system of this type, the thymidine kinase gene of herpes simplex virus type 1 (HSV1-tk) is used to render tumor cells sensitive to the antiviral agent ganciclovir (GCV). Mammalian cells ordinarily are not affected by GCV, because it is not a good substrate for mammalian thymidine kinases. In contrast, the viral thymidine kinase efficiently utilizes ganciclovir as a substrate, which thus is lethally incorporated into the DNA of the cells expressing the viral enzyme. Accordingly, exposure to GCV kills the tumor cells that have taken up and express the viral tk gene. For tumors that display a bystander effect, moreover, non-transformed tumor cells likewise are killed.

By what mechanism(s) a bystander effect occurs is not fully understood. While the inventors do not intend to limit the invention to any particular explanation in this regard, one possible mechanism involves the production in transformed cells of a diffusible form of the sensitizing gene expression product that either acts extracellularly on the chemotherapeutic agent or is taken up by adjacent, non-transformed cells, which thereby become susceptible to the action of agent. It also is possible that one or both of the sensitizing gene expression product and the activated chemotherapeutic agent is communicated between tumor cells, for example, via gap junctions or the uptake of vesicles, produced by a dying cell, which contain the expression product or activated agent.

A variety of tk genes can be used in the present invention. Preferred among these are the tk genes of herpes simplex viruses (HSV), cytomegaloviruses (CMV) and varicella-zoster viruses (VZ).

Heterologous expression of viral thymidine kinases, as described above, confers sensitivity to several nucleoside analogs in addition to ganciclovir, which is a preferred chemotherapeutic agent. Exemplary of other such analogs are acyclovir and 1-2-deoxy-2-fluoro-β-D-arabinofuranosil-5-iodouracil ("FIAU").

In another system the bacterial enzyme cytosine deaminase ("CDA") is used to convert the non-toxic compound 5-fluorocytosine to 5-fluorouracil, which is highly cytotoxic. In this manner, only tumor cells that have taken up and express the CDA gene convert the 5-fluorocytosine to 5-fluorouracil and are killed.

Immune Response-Enhancing Genes:

As explained previously, the present invention takes advantage of a bystander effect to kill even those cells of a targeted tumor that are not transformed to express a foreign sensitizing gene. The goal of eradicating all neoplastic cells in this context can be advanced, in accordance with the present invention, by the use of substances that stimulate or activate the immune system and, thereby, increase the overall percentage of killed neoplastic cells.

The present invention therefore contemplates the use of a retroviral vector that contains at least one gene coding for an immune response-enhancing agent. In the manner described above, such a vector would be introduced into the tumor in the form of whole virus or a retroviral vector-producing cell line. The same vector also could include the sensitizing gene; alternatively, the gene which encodes an immune response-enhancing agent and the sensitizing gene could be introduced into the tumor separately. In either case, the targeted tumor would come to include cells expressing, respectively, a sensitizing gene and a gene that encodes a substance which activates a particular constituent of the immune system or which stimulates the proliferation of certain cells associated with an immune response.

Genes which can be employed in enhancing host immunity to the targeted tumor include those that code for a cytokine and those that encode an immune co-activating signal molecule. In the former category are genes coding for molecules such as TNF, any of interleukins IL-1 through IL-12, the interferons α-IFN, β-IFN and γ-IFN, and a hematopoietic factor like GM-CSF, M-CSF or G-CSF. Illustrative of the latter category of genes is the B7 gene and a gene encoding a class 1 MHC determinant.

Particularly preferred are genes that encode IL-2 or a substance that, like IL-2, is active in recruiting T-cells. It has been found, for example, that transformation of cells in a tumor to effect heterologous expression of a thymidine kinase and human IL-2 results in a regression of the tumor, upon ganciclovir treatment pursuant to the present invention, which is significantly quicker than the tumor regression realized with transformation with the tk gene only.

A given tumor may respond to exposure to several cytokines in concert, for example, a combination of IL-2, IL-4 and GM-CSF. Accordingly, the present invention further contemplates the use of a sensitizing gene, as described above, with a combination of cytokine-encoding genes, introduced into the targeted tumor via the same vector or via a mixture of the different producer cell lines.

Whether such a constellation of cytokines, tailored to the particular tumor under treatment, or a single cytokine is employed, appropriate consideration would be given by the clinician to potential toxic effects of any immune response-enhancing substance. For example, the use of a cytokine gene, as described above, in treating a brain tumor may be unduly toxic and, hence, would be contraindicated.

Delivering Retroviral Vector and Chemotherapeutic Agent to the Tumor:

In accordance with the present invention, a retroviral vector can be transferred into a targeted tumor in situ by direct injection of replication-competent virus, by implantation of a vector producer cell line, or by a combination of both approaches. Such methodology can be employed to deliver a variety of retroviral vectors, carrying virtually any gene, to a variety of tumors at many anatomic sites.

As previously noted, the vector is targeted to tumor cells not only because delivery is tumor-directed per se but also because the cells of a tumor will incorporate the vector and express the sensitizing gene. By contrast, less mitotically active cells of surrounding tissues will be much less susceptible to viral transformation.

Pursuant to an in situ therapeutic modality, the vector preferably would be introduced continuously to a growing tumor in vivo, thereby to insure that retroviral particles would always be in the local environment of the tumor and would infect tumor cells whenever they began DNA synthesis. Continuous local infusion of retroviral vector-containing supernatants, while feasible, is expected to be technically difficult and therefore is not preferred.

Another approach would be to infiltrate the tumor mass with cells engineered to produce retroviral vector particles. The result would be the continuous production of vector within the tumor mass in situ.

After tumor cells are transformed in accordance with the present invention, administration of the chemotherapeutic agent can be effected by any route that results in a therapeutically effective exposure of the tumor to the agent. Methods for delivering the agent include but are not limited to intravenous, intraarterial, subcutaneous, intraperitoneal and intralesional administration. The optimum dosage of the agent will vary with the particular case, and relevant pharmacokinetics will be determined routinely in the clinical context.

Preferred Tumor Targets:

The therapeutic approach of the present invention should be particularly useful when the targeted tumor is in a tissue made up of cells which are relatively quiescent mitotically, such as liver, skin, bone, muscle, bladder, prostate, kidney, adrenal, pancreas, heart, blood vessel and thyroid tissues, among others. The inventive approach also should be useful against tumors located in the subarachnoid space, in the peritoneum, and in the pleural cavity. Conversely, tissues in which there are many mitotically active cells, including gut, spleen, thymus and bone marrow, are less preferred targets.

In addition, tumors in organs the loss of which, in whole or part, is generally well-tolerated are preferred targets of a treatment according to the present invention. Liver is preferred in this respect, for instance, because large portions of that organ can be removed from a patient without significantly impairing health.

Primary and metastatic tumors which can be treated in accordance with the present invention include but are not limited to those that occur in adrenal, bladder, bone, breast, cervix, endocrine gland (including thyroid and pituitary glands), gastrointestinal (esophagus, stomach, intestine, colorectal, etc.), heart, hematopoietic, kidney, liver, lung, muscle, nervous system (including brain and eye), oral cavity, pharynx and larynx, ovarian, pancreas, penile, prostate, skin, testicular, thymoma and uterine tissues.

Particularly preferred targets are brain tumors, which display several features making them especially susceptible to treatment in accordance with the present invention. Neurons and most other stationary cells brain are quiescent and do not regularly synthesize DNA. Vascular endothelial cells in the brain may be cycling at a low rate, but among those most likely to be in cycle would be cells responding to angiogenesis promoting signals often localized in the in the vicinity of a tumor. Such vessels would most likely be part of the blood supply of the tumor and therefore their destruction would also be desirable. Within the brain, therefore, the principal mitotically active cells would be tumor cells or cells necessary for its support. Accordingly, retroviral vectors introduced into the brain principally will integrate into and affect only tumor cells or cells connected with tumor vascularization.

Brain tumors often are localized and yet are inoperable because of their location in relationship to adjacent critical structures. Accordingly, a technique within the present invention, whereby delivery of a toxic product to the tumor is effected without surgical resection, is very useful. Another advantage of targeting brain tumors in the present invention is that the brain is an immunologically privileged site and, thus, may permit retroviral vector-producer cells which are histoincompatible to persist for a significant period without immunologic rejection.

Direct injection also minimizes undesirable propagation of the virus in the body, especially when replication-competent retroviral vectors are used. Since most cells of the body express receptors for amphotropic retroviral vectors, any vector particle which escapes from the local environment of the tumor should immediately bind to another cell. Most cells are not in cycle, however, and therefore will not integrate the genes carried by the vector and will not express any genes which it contains. Thus, the proportion of potential target cells which are in cycle at the time of exposure will be small, and systemic toxic effects to normal tissues will be minimized.

Without further elaboration, it is believed that those skilled in the art, informed by the preceding description, can utilize the present invention fully. The following examples therefore are presented for purposes of illustration only.

EXAMPLE 1

Retroviral vector-mediated gene-transfer occurring in vivo after reimplantation of mixtures of tumor cells with vector-producing fibroblasts Mice were inoculated subcutaneously with a fibrosarcoma mixed with either NeoR-expressing control 3T3 cells which do not produce retroviral vector [group 1] or NeoR retroviral vector-producing 3T3 (PA317) cells [group 2]. To quantify the efficiency of gene transfer in vivo, the tumors were resected after four weeks, reestablished in culture, and then tested in a clonogenic assay for expression of NeoR.

Clonogenic assays were carried out, as described below, for the presence of NeoR-expressing tumor cells in mice previously injected with mixtures of untransduced tumor and fibroblasts which produced NeoR gene-containing retroviral vectors.

One million murine fibrosarcoma (MCA 205) cells mixed with an equal number of murine fibroblasts were injected subcutaneously into syngeneic, female C57BL/6 mice (6 to 8-weeks old). Group 1 received tumor cells and 3T3 cells transduced with the retroviral vector LNL6 (NeoR non-producer). Group 2 was given tumor cells mixed with LNL6 retroviral vector producing PA317 fibroblasts. LNL6 produced a NeoR-containing, replication competent virus-free retroviral vector with a titer of $-10^6$/ml. Tumors grew in 100% of the animals.

After four weeks the tumors were harvested from three mice in each group, were recultured, and were tested for transfer of Neomycin resistance in a clonogenic assay at 500 cells/well seeded in a six-well microculture plate±1.0 mg/ml G418. The number of growing colonies was enumerated at seven days. The cloning efficiency of tumor cells from each group cultured in the absence of G418 was 8–22% (data not shown).

The results of the experiment are summarized in TABLE 1. No G418-resistant tumor colonies were recovered from any animal in group 1. By contrast, a mean of 63% of the tumor cells recovered from animals injected with tumor mixed with retroviral vector-producing fibroblasts [group 2] grew as G418 resistant colonies, indicating that in vivo gene transfer into the proliferating tumor cells had occurred.

Southern blot analysis for the NeoR vector and direct enzyme assay for neomycin phosphotransferase (NPT) were positive in all these G418 resistant tumor cell populations [data not shown]. These experiments demonstrated that proliferating tumor cells could be transduced in vivo successfully if mixed with retroviral vector producing cells.

EXAMPLE 2

Fibroblasts transformed with a retroviral vector to express HSV-tk can mediate ganciclovir killing of adjacent tumor cells that have not been transduced by the vector Mice were injected subcutaneously with mixtures of tumor cells and control fibroblasts or fibroblasts engineered to produce HSV-tk retroviral vectors. Three days after cell implantation small growing tumors became visible and ganciclovir treatment twice daily was begun. The results are shown in FIG. 2. In control animals, bearing tumors mixed with control fibroblasts or fibroblasts producing a NeoR vector, GCV treatment had no effect on the growth of the tumors. By contrast, in animals carrying tumors derived from the mixtures of tumor cells with HSV-tk retroviral vector-producing fibroblasts the tumors regressed rapidly and completely with GCV treatment, and the animals remained tumor free until the experiment was terminated at day 29. This result was striking and unexpected, since the efficiency of in vivo gene transfer to tumor in this type of mixture experiment was less than 100%, as evidenced by the results in TABLE 1.

EXAMPLE 3

GCV mediated complete tumor regression in animals injected with 50:50 or 90:10 mixtures of tumor cells and HSV-tk transformed tumor cells Adult C57L6 mice were injected subcutaneously with a total of $1\times10^5$ tumor cells, presented as a mixture of various proportions of wild type and HSV-tk-transduced cells. The tumor cells studied included the murine fibrosarcomas 102 and 205 and the murine adenocarcinoma 38. There were five mice in each group and there were no differences among the groups with respect to the HSV-tk-mediated bystander effect. Beginning on day 4 after tumor injection, each animal was treated with 3 mg of ganciclovir i.p. twice daily for seven days.

The results of the experiments are presented in TABLE 2. The incidence of tumors in groups of mice not treated with

TABLE 1

Clonogenic assay results for tumor cell regrown from mice four weeks post-inoculation with tumor cells and/or producer cells.

| Tx Group[1] | No. of Mice | Pre-selection in G418[2] | Tumor Cells No G418 | G418 1.0 mg/ml | % Positive Colonies[3] |
|---|---|---|---|---|---|
| None (tumor alone) | 3 | No | 116 ± 7 | 0 | 0 |
| Tumor + 3T3/LNLS | 3 | No | 81 ± 3 | 0 | 0 |
| Tumor + LNL6 Prod. | 3 | No | 75 ± 30 | 49 ± 23 | 65% |
| Tumor + LNL6 Prod. | 3 | Yes | 91 ± 11 | 92 ± 19 | 100% |

[1]$2 \times 10^8$ cells were injected into each mouse. Mixtures of tumor cells and 3T3/LNL6 or LNLG producers were 1:1.
[2]Tumors were excised 4 weeks after injection and single suspensions placed in culture. A portion of the cells were then selected in 1.0 mg/ml G418 for 7 days prior to the assay (marked YES). The non-selected and selected cells were then cloned et 500 cells/well in 12 well plates ± 1.0 mg/ml G418. The number of surviving colonies were counted and are expressed as the means ± SD.
[3]The tumor and LNL6 transduced 3T3 cells were negative for colony growth. This suggests that the 3T3 cells were unable to survive for 4 weeks in vivo. In contrast, the producer cells were 65% G418 positive. This was increased to 100% with G418 selection prior to cloning.
65% of the tumor cells recovered from mice 4 weeks after they were injected with mixtures of retroviral vector producer cells and "gene negative" tumor cells had acquired the NeoR gene and were resistant to G418. With selection for NeoR expressing cells by G418, 100% of the recovered cells survived in the clonogenic assay.

GCV was similar whether or not they had been transduced with the HSV-tk gene. After five weeks of observation, less than 15% of the GCV treated mice given mixtures consisting of 50% wild type and 50% HSV-tk cells had developed tumors. Mice given tumor mixtures with as little as 10% HSV-tk containing cells developed tumors in less than 50% of the animals.

Even with significantly less than 100% transduction of all of the malignant cells in the tumor mass, therefore, HSV-tk gene transfer was sufficient for complete tumor eradication in vivo. A bystander effect associated with the transformed tumor cells accounts for the GCV-mediated killing of untransformed tumor cells. It is notable that nearby normal tissues were affected only minimally, i.e., normal skin overlying the tumors and muscles underlying them were not visibly damaged when the tumor was completely destroyed during GCV treatment.

TABLE 2

The effect of ganciclovir treatment on the incidence of tumor growth in mice injected with mixtures consisting of various proportions of HSV-*tk* gene transduced and wild type tumor cells.

| Tumor Mixture Recipient* | | Incidence of Palpable Tumors | |
| --- | --- | --- | --- |
| % wild type | % HSV-tk tumor | 2 weeks | 5 weeks |
| 0% | 100% | 0/15 | 2/15 |
| 50% | 50% | 0/15 | 1/15 |
| 90% | 10% | 3/15 | 6/15 |
| 100% | 0% | 12/15 | 15/15 |

EXAMPLE 4

Direct in situ injection of HSV-tk retroviral vector-producing murine fibroblasts into an implanted 9L gliomsarcoma caused regression of the established cancer Fisher 344 rats weighing 230–350 grams were anesthetized with ketamine and placed in a stereotactic apparatus. $4 \times 10^4$ "19L" syngeneic gliosarcoma cells were inoculated into the right cerebral hemisphere, a dose of tumor which results in 100% lethality by 3–4 weeks.

Five days later, the same stereotactic coordinates were used to directly inject saline, $3-5 \times 10^6$ 3T3/HSV-tk non-producer cells or PA317/HSV-tk producer line cells into the growing "9L" tumor.

After five more days, treatment was instituted with intraperitoneal injections of ganciclovir at 150 mg/kg twice daily for five days. The rats then were sacrificed to determine anti-tumor effect.

In recipients in which the gliomas were injected with saline or control non-vector producing fibroblasts, GCV treatment had no effect on the growth of the tumors, which had rapidly progressed in size and were growing out of the brain along the needle tract. In striking contrast, rats injected with tk-producer cell lines demonstrated complete regression of the tumors both macroscopically and microscopically, with replication-incompetent vector alone and with a combination of replication-incompetent and competent vector producer by the implanted producer cells.

Adjacent brain tissue, which is replicatively quiescent and which should not integrate the retroviral vector or express the HSV-tk enzyme, in fact was not harmed.

These data show the successful transduction of a tumor in vivo using direct injection of the tumor with murine retroviral vector producer cell lines. The direct injection of murine fibroblasts producing a HSV-tk vector into growing brain tumors, followed by treatment with GCV, resulted in complete elimination of the implanted tumor.

EXAMPLE 5

Injection of retroviral producer cells and subsequent GCV treatment does not damage normal tissue in mice Retroviral producer cells were injected intravenously and into the abdomen of mice, and one week later the mice were treated with GCV. The mice were sacrificed one week following completion of GCV treatment, and the organs were examined for evidence of damage. There was no evidence of damage to the gut, thymus, lung, liver, spleen or bone marrow.

What we claim is:

1. A method of treating a tumor comprising a plurality of tumor cells in a subject, comprising:
    (a) determining ex vivo that the tumor cells exhibit a bystander effect in response to exposure to a selected cytotoxic drug;
    (b) directly administering to the tumor a plurality of fibroblasts containing a retroviral vector which includes a gene selected from the group consisting of an HSV-thymidine kinase gene and a cytosine deaminase gene, wherein the gene is expressed in at least some of the tumor cells; and
    (c) delivering a suitable pro-drug to the tumor wherein expression of the gene results in conversion of the pro-drug to the cytotoxic drug, thereby killing tumor cells in which the gene is expressed and neighboring tumor cells in which the gene is not expressed.

2. The method of claim 1 wherein the tumor is a brain tumor.

3. The method of claim 1 wherein the gene is an HSV-thymidine kinase gene and the pro-drug is a suitable nucleoside analog.

4. The method of claim 3 wherein the pro-drug is acyclovir, ganciclovir or 1-2-deoxy-2-fluoro-β-D-arabinofuranosil-5-iodouracil.

5. The method of claim 1 wherein the gene is cytosine deaminase and the pro-drug is 5-fluorocytosine.

* * * * *

UNITED STATES PATENT AND TRADEMARK OFFICE
CERTIFICATE OF CORRECTION

PATENT NO.   : 6,045,789
DATED        : April 4, 2000
INVENTOR(S)  : Culver et al.

It is certified that error appears in the above-identified patent and that said Letters Patent is hereby corrected as shown below:

Title page,
Inventors, "Kenneth W. Culver, Potomac; R. Michael Blaese, Rockville, Both of Md." should read -- Kenneth W. Culver, Des Moines, Ia.; R. Michael Blaese, Rockville, Md. --.

Column 11,
Line 19, "of-$10^6$/ml." should read -- of ~ $10^6$/ml. --.
Line 54, TABLE 1, "$^1$2x$10^8$ cells" should read -- $^1$2x$10^6$ cells --.
Line 54, TABLE 1, "LNLG" should read -- LNL6 --.
Line 58, TABLE 1, "cloned et 500 cells/well" should read -- cloned at 500 cells/well --.

Column 13,
Line 42, "19L" should read -- 9L --.

Signed and Sealed this

Fourth Day of December, 2001

Attest:

NICHOLAS P. GODICI
Attesting Officer   Acting Director of the United States Patent and Trademark Office